United States Patent [19]
Dürholz et al.

[11] 3,931,255
[45] Jan. 6, 1976

[54] PROCESS FOR THE PRODUCTION OF 5-NITRO-1,4-NAPHTHOQUINONE

[75] Inventors: Friedrich Dürholz, Remscheid; Rolf Pütter, Duesseldorf, both of Germany

[73] Assignee: Bayer Aktiengesellschaft, Leverkusen, Germany

[22] Filed: Nov. 27, 1974

[21] Appl. No.: 527,797

[30] Foreign Application Priority Data
Dec. 1, 1973  Germany............................ 2359950

[52] U.S. Cl.............................. 260/396 R; 260/575
[51] Int. Cl.².......................................... C07C 76/02
[58] Field of Search......................... 260/396 R, 575

[56] References Cited
OTHER PUBLICATIONS
Migridichian, Org. Syn., 1957, p. 1426.

*Primary Examiner*—Vivian Garner
*Attorney, Agent, or Firm*—Burgess, Dinklage & Sprung

[57] ABSTRACT

5-Nitro-1,4-naphthoquinone is prepared by reducing 8-nitro-1,4-naphthoquinone-1-oxime and/or 5-nitro-1,4-naphthoquinone-1-oxime in an aqueous and/or organic reaction medium in the presence of iron (II) ions and a hydrogen halide at a temperature in the range of from $-20°$ to $100°C$, and thereafter oxidizing the 8- and and/or 5-nitro-4-amino-1-naphthol formed, or the corresponding salt, optionally without intermediate isolation, at a temperature in the range of from $-10°$ to $100°C$ to form the desired 5-nitro-1,4-naphthoquinone.

6 Claims, No Drawings

PROCESS FOR THE PRODUCTION OF 5-NITRO-1,4-NAPHTHOQUINONE

This invention relates to a particularly advantageous process for the production of 5-nitro-1,4-naphthoquinone from 8-nitro-1,4-naphthoquinone-1-oxime and/or 5-nitro-1,4-naphthoquinone-1-oxime.

The selective reduction of 8-nitro-1,4-naphthoquinone-1-oxime into 5-nitro-4-amino-1-naphthol is already known (Zh. Vses. Khim. Obshch. 5 (1969), pages 474 to 475). The selective reducing agent used for this reaction is phenyl hydrazine which can only be obtained by a multistage process and which, in addition, is toxic. Furthermore, the presence of phenyl hydrazine gives rise to the formation of secondary products which necessitate extensive purification. Accordingly, the known process is not suitable for working on an industrial scale.

It has now been found that 5-nitro-1,4-naphthoquinone can be obtained by a particularly advantageous process in which 8-nitro-1,4-naphthoquinone-1-oxime and/or 5-nitro-1,4-naphthoquinone-1-oxime is/are reduced in an aqueous and/or organic reaction medium in the presence of iron (II) ions and hydrogen halide at temperatures in the range of from −20°C to +100°C, and the resulting 8- and/or 5-nitro-4-amino-1-naphthol and the corresponding salt are oxidized, optionally without intermediate isolation, at temperatures in the range of from −10° to +100°C to form the 5-nitro-1,4-naphthoquinone.

The reduction in the presence of iron (II) ions and hydrogen halide is preferably carried out at temperatures in the range of from −5° to 70°C, more especially at temperatures in the range of from 10° to 45°C. Oxidation is preferably carried out at temperatures in the range of from 20° to 80°C and more especially at temperatures in the range of from 40° to 60°C.

8- and 5-Nitronaphthoquinone oxime are known (Friedlander, Vol.4, pages 342 to 344; C. Graebe, A. Oser, Ann.335 (1904), pages 143 et seq; Zh. Vses. Khim. Obshch. 5 (1969), pages 474 to 475).

In the context of the invention, 8- and 5-nitronaphthoquinone oxime are 8-nitro-1,4-naphthoquinone-1-oxime and 5-nitro-1,4-naphthoquinone-1-oxime and their tautomeric forms, 5-nitro-4-nitroso-1-naphthol and 8-nitro-4-nitroso-1-naphthol, and also a mixture of the tautomeric forms.

The process according to the invention is illustrated by the following example:

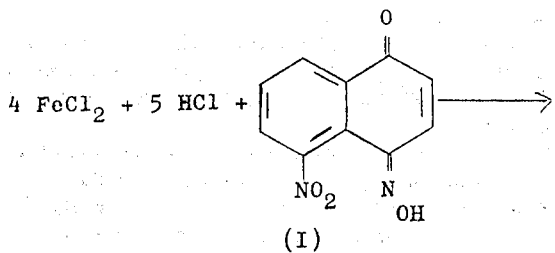

Reduction into 8- and/or 5-nitro-4-amino-1-naphthol requires 4 reduction equivalents which, in the process according to the invention, can be completely supplied by iron (II) ions. The iron (II) ions are added in the form of iron (II) salts, such as $FeCl_2$, $FeCl_2 \cdot 4H_2O$ and $FeSO_4 \cdot 7H_2O$.

However, the iron (II) ions or salts can also be partly replaced by reducing agents which, under the conditions applied in the process according to the invention, reduce iron (III) ions into iron (II) ions. Reducing agents of this kind are, for example, base metals such as iron, zinc or tin; non-metallic reducing agents such as sulphur dioxide and phosphorus in the presence of catalytic quantities of hydrogen iodide; and metal ions of the kind whose reduction potential is greater than that of the iron (II)) ions, such as tin (II) ions.

Where reference is made both in the foregoing and hereinafter to ions, it is obvious that these ions do not exist alone, but require an oppositely charged ion which does not have to be of any particular type. Preferred oppositely charged ions are halogen and, in particular, chlorine ions.

From 0.01 to about 6 mols and preferably from 1 to 4.4 mols of iron (II) ions or salts are generally used per mol of 8-nitro-1,4-naphthoquinone-1-oxime and/or 5-nitro-1,4-naphthoquinone-1-oxime in the process according to the invention.

In cases where only iron (II) ions or salts are used as reducing agents in the process according to the invention, it is necessary to use at least the stoichiometrically necessary quantity of 4 mols per mol of 8-nitro-and/or 5-nitro-1,4-naphthoquinone-1-oxime. Where other reducing agents are used as well, the quantity of iron (II) ions can be reduced to catalytic quantities, generally to 0.01 and more especially to 2 mols of iron (II) ions per mol of compound to be reduced. Where other strong reducing agents are used, such as iron, zinc, tin or tin (II) ions, they may be employed in a quantity of up to 4 reduction equivalents and preferably in a quantity of up to 2 reduction equivalents per mol of starting compound to be reduced. For example, it is possible to employ two equivalents of a strong reducing agent and 2 mols of iron (II) ions or salts.

In cases where iron (II) ions alone are used or where iron (II) ions are employed together with other, weak reducing agents, such as sulphur oxide and phosphorus in the presence of catalytic quantities of hydrogen iodide, an excess beyond the stoichiometrically necessary quantity of reducing agent may be employed without any disadvantages. This excess may amount to 200 percent by weight and, more especially to 20 percent by weight of the necessary quantity.

In general, the hydrogen halide is used in at least the stoichiometrically necessary quantity of 5 mol per mol of starting compound to be reduced. However, it can be advantageous to use an excess of up to 20 mols of hydrogen halide. It is possible, but not necessary, to use an even larger excess of hydrogen halide.

Some of the stoichiometrically necessary hydrogen halide may be replaced with advantage by other strong, non-oxidizing mineral acids, for example sulphuric acid or phosphoric acid. In the complete absence of halogen ions, reduction is very slow, so that very low conversions, if any, are obtained (cf. Comparison Example 24).

Suitable hydrogen halides include hydrogen fluoride, hydrogen chloride and hydrogen bromide. Hydrogen chloride is preferably used.

The process according to the invention can be carried out both in a pure aqueous reaction medium and also in an organic reaction medium.

Preferred aqueous reaction media are aqueous mineral acids, for example sulphuric acid (more especially 35 to 70 percent by weight sulphuric acid), hydrochloric acid (more especially 20 to 42 percent by weight hydrochloric acid), hydrobromic acid (more especially 20 to 48 percent by weight hydrobromic acid) and phosphoric acid (more especially 40 to 90 percent by weight phosphoric acid).

Organic solvents or solutions and/or mixtures of organic solvents and water and, optionally, aqueous acids, may be used with advantage as organic reaction media.

Of the organic solvents, it is particularly preferred to use aliphatic carboxylic acids such as formic acid, acetic acid and propionic acid. It is also possible to use nitriles such as acetonitrile and propionitrile; ketones such as acetone and methyl ethyl ketone; alcohols such as methanol, ethanol, isopropanol, butanols, ethylene glycol and propylene glycol; ethers such as diethyl ether, tetrahydrofuran, dioxan, ethylene glycol monoalkyl ether and ethylene glycol dialkyl ether (alkyl $C_1 - C_4$); carboxylic acid esters such as acetic acid ethyl ester or acetic acid butyl ester; lactones, such as $\gamma$-butyrolactone; and sulphones such as sulpholan. Finally, it is also possible to use carboxylic acid amides such as dimethyl formamide, N-methyl pyrrolidone and pyrrolidone.

In general, the process according to the invention is carried out as follows: 8- and/or 5-nitronaphthoquinone-1-oxime are dissolved or suspended in the selected reaction medium. The iron (II) salt is then added either as such or in solution and the reaction is carried out at the selected reaction temperature by the addition of hydrogen halide in the form of a gas or in the form of aqueous hydrohalic acid. In cases where the reaction medium already contains hydrogen halide, the reaction begins on addition of the iron (II) salt. However, the order in which the individual reaction components are added can be changed as required and, for example, the iron (II) salt and hydrogen halide may be initially introduced in solution and/or suspension in the reaction medium selected, followed by addition of the nitronaphthoquinone oxime.

The reaction components may each be added in batches, in portions or continuously. It is also possible, preferably in cases where the reaction is carried out continuously, to introduce all the reaction components continuously at the same time.

The process according to the invention can be carried out both under normal pressure and also under reduced or elevated pressure. In general, the process is preferably carried out under normal pressure.

In cases where ketones are present as organic solvents in the reaction medium, the 8- and/or 5-nitro-4-amino-1-naphthol formed can be further reacted with the ketone to form the corresponding Schiff's base, especially where only a little water is present in the reaction medium, and the Schiff's base thus formed may even be isolated. However, the Schiff's base formed is generally split again by hydrolysis during subsequent oxidation to form the 5-nitro-1,4-naphthoquinone, and accordingly, can be used in the same way as 5-nitro-4-amino-1-naphthol in the following oxidation stage.

The 5- and/or 8-nitro-4-amino-1-naphthol formed by reduction in the first stage, or the corresponding salt, may be isolated on completion of the reaction and oxidized in a second, separate reaction stage to form 5-nitro-1,4-naphthoquinone.

In general, known oxidants may be used for the oxidation stage. In particular it is possible to use oxidants of the kind normally used for the oxidation of hydroquinones or those aminophenols or aminonaphthols structurally related to hydroquinones (Beilstein VII, pages 709, 724 et seq, 733; Supplementary Volume I, pages 384 et seq, Supplementary Volume II, pages 645, 651; Beilstein VII, pages 599, 609; Supplementary Volume I, pages 337, 340; Supplementary Volume II, page 566).

The following are mentioned as examples of oxidants: iron (III) and copper (II) halides, potassium permanganate and manganese dioxide;

chromic acid and its salts such as chromates and bichromates, more especially of the alkali metals, salts of the oxyacids of chlorine, such as sodium chlorate, in combination with compounds of vanadium such as $VCl_3$, $V_2O_5$ and ammonium vanadate and/or iron salts such as $FeSO_4.7H_2O$, $FeCl_2.4H_2O$ and/or copper halides such as $CuCl_2$;

hydrogen peroxide and peroxo compounds such as peroxobisulphate, more especially in the presence of halides of iron and copper; and oxidation systems such as nitric acid, nitrous acid and their salts, $NO_2$, $N_2O_3$, nitrous gases, more especially in hydrchloric acid reaction media and in the presence of iron salts or copper salts.

In some cases, it is also possible to use air and other oxygen-containing gases, and also oxygen itself, for regenerating other oxidants which may then also be used in less than equivalent or in catalytic quantities.

The 5-nitro-1,4-naphthoquinone formed can be isolated from the reaction mixture in the usual way.

In one preferred embodiment of the process according to the invention, reduction of the 5- and/or 8-nitro-1,4-naphthoquinone-1-oxime is carried out with at least the equivalent quantity of iron (II) ions, preferably with from 4 to 5 mols of iron (II) ions per mol of oxime. In this way, the subsequent oxidation stage may be carried out with particular advantage. The 8- and/or 5-nitro-4-amino-1-naphthol formed by reduction, which is present as the salt form in an acid reaction medium, may be oxidized in a particularly simple manner, without intermediate isolation, in the reaction mixture. The reaction medium is diluted with water and the oxidation effected by the iron (III) salt simultaneously formed as secondary reaction product, because the increase in the redox potential of the iron (III) salt or reduction in the redox potential of the 5-nitro-4-aminonaphthol salt required for oxidation can be obtained simply by dilution with water. The minimum quantity of water required for diluting the reaction mixture is governed both by the type and quantity of acids used and by the type and quantity of solvent employed. It can readily be determined from the known physico chemical data or by one or more preliminary tests.

This particular embodiment of the process according to the invention may, with advantage, be modified to the extent that the minimum of four reduction equivalents required for reduction can be used in the form of 2 mols of iron (II) salt and two reduction equivalents of another suitable reducing agent, such as tin (II) chloride or sulphur dioxide, in the presence of catalytic quantities of hydrogen iodide or agents forming hydrogen iodide, or in the form of 1 mol of iron (II) salt and 1 g-atom of metallic iron.

The 5-nitro-1,4-naphthoquinone obtained can be isolated from the reaction mixture in the usual way.

The mother liquor left following separation of the 5-nitro-1,4-naphthoquinone, which contains iron (III) ions and, optionally, even iron (II) ions in addition to iron (III) ions, may advantageously be reduced in known manner, for example by treatment with hydrogen or sulphur dioxide, and an iron (II) salt subsequently isolated from the resulting iron (II) salt solution by crystallization and reused, optionally following the removal by distillation of the organic solvent used and/or of the hydrohalic acid and/or water. The concentrated iron (II) salt solution obtained following the removal by distillation of the organic solvent and/or of the hydrohalic acid and/or of water may with advantage be directly used for further reductions.

By comparison with the known process, the process according to the invention gives better yields of more pure 5-nitro-naphthoquinone in a particularly simple manner. It is known that nitro groups on the aromatic nucleus are readily reduced into amino groups by iron (II) ions in acid medium. Accordingly, it is particularly surprising that it is possible by the process according to the invention to carry out reduction selectively in the case of the 5- and/or 8-nitronaphthoquinone oxime.

5-Nitronaphthoquinone can be converted in known manner into 1-nitroanthraquinone by butadiene addition and dehydrogenation of the adduct formed. The 1-nitroanthraquinone can be reduced into 1-aminoanthraquinone which is an important starting material for dyes. It is possible in this way to produce a pure 1-nitroanthraquinone, whilst nitration of anthraquinone into 1-nitroanthraquinone results in the formation of a mixture of different nitro derivatives which is difficult to separate.

In the following Examples, the percentages quoted are percentages by weight unless otherwise stated. Where contents are specified in respect of mineral acids, the remainder is water.

EXAMPLES 1 to 12

42 g (0.21 mol) of iron (II) chloride tetrahydrate and 11 g (0.05 mol) of 8-nitro-1,4-naphthoquinone-1-oxime are introduced into 120 ml quantities of the solvents indicated in Table I below. While gaseous hydrogen chloride is slowly passed through them, the mixtures are left to react with continuous stirring at the temperatures indicated in Table I below until the respective reactions are complete. The increases in weight indicated in Table I below are obtained. After the reaction times specified in Table I, the mixtures are poured onto 500 ml of water heated to approximately 40°C, followed by stirring for 30 minutes. The 5-nitro-1,4-naphthoquinone formed is filtered off under suction, washed off under suction, washed with water until neutral and dried at 50°C. The yields of 5-nitro-1,4-naphthoquinone specified in Table I below in g and percent of the theoretical yield are obtained.

TABLE I

| Example No. | Solvent | 5-Nitro-naphthoquinone (g) | (% of theoretical) | Melting Point °C | Reduction Time (hours) | Temperature (°C) | Increase in Weight (g) |
| --- | --- | --- | --- | --- | --- | --- | --- |
| 1 | acetic acid | 8.7 | 85 | 158 | 1 | 30 | 27 |
| 2 | i-propanol | 9.6 | 94 | 163 | 3 | 15 – 20 | 35 |
| 3 | methanol | 9.2 | 90 | 160 | 5 | approx.20 | -* |
| 4 | ethylene glycol | 8.6 | 84 | 160 | 3 | 15 – 20 | 18 |
| 5 | acetone | 9.2 | 90 | 161 | 1 | 15 – 20 | 33 |
| 6 | acetone | 9.0 | 88 | 162 | 2.5 | 0 – 5 | -* |
| 7 | methylethyl ketone | 9.5 | 93 | 163 | 2 | 30 – 35 | -* |
| 8 | tetrahydrofuran | 9.0 | 88 | 160 | 3 | approx.0 | -* |
| 9 | N-methyl pyrrolidone | 9.5 | 93 | 160 | 1.5 | approx.0 | -* |
| 10 | propionic acid(70%) | 9.0 | 88 | 162 | 2 | approx.40 | -* |
| 11 | γ-butyrolactone | 8.8 | 86 | 160 | approx.5 | 5 – 10 | 25 |
| 12 | diethylene glycol dimethyl ether | 9.6 | 94 | 162 | 3 | 15 – 20 | 18 |

*=not determined

EXAMPLES 13 to 16

A suspension of the quantities indicated in Table II below of iron (II) chloride tetrahydrate in 120 ml of 37 percent by weight aqueous hydrochloric acid is saturated by the introduction of approximately 10 g of hydrogen chloride gas. 11 g (0.05 mol) of 8-nitro-1,4-naphthoquinone-1-oxime are added at the reaction temperature indicated in Table II below, and the reaction mixture is left to react with stirring for 1.5 hours at the temperature specified. The quantity indicated in Table II below of the particular reducing agent is then introduced in small portions over a period of about 1.5 hours, and the mixture is left to react for 3 hours. The reaction mixture is then poured into approximately 1,000 ml of water heated to approximately 40°C, and left to react for 1 hour. The 5-nitro-1,4-naphthoquinone precipitated is filtered off under suction, washed with water until neutral and dried at approximately 50°C. The yield obtained is indicated in Table II below.

drate are heated to reflux temperature in 100 ml of methyl ethyl ketone. 25 g of hydrogen chloride gas are then introduced over a period of 20 minutes during which the sump temperature is kept at 87° to 90°C. The reaction mixture is stirred for another hour at this temperature, after which it is poured into 1000 ml of water heated to approximately 50°C, followed by stirring for 30 minutes at that temperature. The reaction product precipitated is then filtered off under suction. Recrystallization from toluene following the addition of 2 g of active carbon gives 4 g (78 percent of the theoretical yield) of 5-nitro-1,4-naphthoquinone melting at 164°C.

Table II

| Example No. | Quantity of iron chloride (g) | | Temperature (°C) | 5-nitro-1,4-naphthoquinone (g) (% of theoretical) | | Melting Point (°C) |
|---|---|---|---|---|---|---|
| 13 | 15 | Fe (2.8 g) | approx. 0 | 8.5 | 83 | 160 |
| 14 | 23 | $Na_2SO_3$ (6.3 g) | approx. 0 | 8.4 | 82 | 163 |
| 15 | 23 | Sn (2.9 g) | 15 – 20 | 8.6 | 84 | 160 |
| 16 | 23 | $SnCl_2.2H_2O$(11.3 g) | 15 – 20 | 8.1 | 79 | 161 |

EXAMPLE 17

11 g of 8-nitro-1,4-naphthoquinone-1-oxime and 30 g (0.21 mol) of $FeCl_2.H_2O$ are suspended in 100 ml of acetonitrile. The suspension is cooled to 5°C in an ice bath, after which approximately 25 g of hydrogen chloride gas are slowly introduced with stirring at 5° to 10°C. After 2 hours, 350 ml of water are added, followed by stirring for 1 hour at room temperature. The crystalline 5-nitro-1,4-naphthoquinone precipitated is then filtered off, washed with water until neutral and dried at 50°C. Crystals melting at 165°C are obtained in a yield of 9.7 g or 95 percent of the theoretical yield.

EXAMPLE 18

120 ml of 37 percent by weight aqueous hydrochloric acid and 42 g (0.21 mol) of iron (II) chloride tetrahydrate are introduced into a reaction vessel and saturated with approximately 8 g of gaseous hydrogen chloride. 11 g of 5-nitro-1,4-naphthoquinone-1-oxime are introduced at a temperature of about 20° to 25°C. The reaction mixture is kept at the temperature indicated with stirring and, after 2 hours, is poured into 1,000 ml of water heated to approximately 40°C. followed by stirring for 30 minutes. The reaction product precipitated is then filtered off under suction, washed with water until neutral and dried at approximately 50°C. 5-Nitro-1,4-naphthoquinone melting at 161°C is thus obtained in a yield of 9.8 g (96 percent of the theoretical yield).

EXAMPLE 19

5.5 g (0.025 mol) of 8-nitro-1,4-naphthoquinone-1-oxime and 21 g (0.11 mol) of iron (II) chloride tetrahy-

EXAMPLES 20 to 25

11 g of 8-nitro-1,4-naphthoquinone-1-oxime and the quantity, indicated in Table III below, of the particular iron (II) salt are left to react in 120 ml of the mineral acid indicated with the concentration specified at the particular temperature quoted, and at the same time the quantity of hydrogen chloride gas indicated is introduced over the period specified in Table III below. After the reaction time specified, the reaction mixtures are poured into 1,000 ml of water heated to approximately 60°C, followed by stirring for 1.5 hours at that temperature. The reaction product precipitated is then filtered off under suction, washed with water until neutral and dried at 50°C. The yield of reaction product (5-nitro-1,4-naphthoquinone) and its content of unreacted 8-nitro-1,4-naphthoquinone-1-oxime in percent by weight are given in the last two columns of Table III below.

Examples 23 to 25 are Comparison Examples.

Table III

| Example No. | Acid | Iron(II) salt | Temperature (°C) | Time (hours) | HCl gas (g) | Reaction product (g) | Content of unreacted oxime in % |
|---|---|---|---|---|---|---|---|
| 20 | $H_2SO_4$ | $FeCl_2.4H_2O$(42g) | 10 – 20 | 55 | approx.25 | 9.4 | approx. 0% |
| 21 | $H_2SO_4$ (55%) | $FeCl_2.4H_2O$(42g) | 30 | approx.4 | 17.5 | 9.8 | approx. 8% |
| 22 | $H_3PO_4$ (50%) | $FeCl_2.4H_2O$(42g) | 10 – 20 | approx.5 | approx.25 | 9.6 | approx. 0% |
| 23 | $H_3PO_4$ (85%) | $FeCl_2.4H_2O$(42g) | 40 | 5.5 | 0 | 8.5 | approx.40% |
| 24 | $H_3PO_4$ (85%) | $FeSO_4.7H_2O$(61g) | 40 | 5.5 | 0 | 10.2 | approx.92% |
| 25 | $H_2SO_4$ (60%) | $FeSO_4.7H_2O$(61g) | 40 | 5.5 | 0 | 10.5 | approx.100% |

EXAMPLE 26

5.5 g of 8-nitro-1,4-naphthoquinone-1-oxime are suspended in 450 ml of 38 percent by weight aqueous hydrochloric acid, followed by heating to 33°C. 61 g (0.22 mol) of iron (II) sulphate heptahydrate are then introduced in portions with stirring. After 1.5 hours, the reaction mixture is poured into 1000 ml of water heated to approximately 50°C, followed by stirring for 1 hour at that temperature. The reaction product precipitated is filtered off under suction, washed with water until neutral and dried at approximately 50°C. The yield amounts to 4 g (78 percent of the theoretical yield) of 5-nitro-1,4-naphthoquinone melting at 160°C.

EXAMPLE 27

11 g of 8-nitro-1,4-naphthoquinone-1-oxime and 42 g (0.21 mol) of iron (II) chloride tetrahydrate are suspended with stirring in 100 ml of acetone, and the resulting suspension is heated to reflux temperature. 25 g of hydrogen chloride gas are then introduced for 20 minutes, during which a sump temperature of approximately 70°C is maintained. The reaction mixture is then stirred for about 10 minutes at that temperature, followed by cooling to approximately 0°C. At this temperature, more hydrogen chloride gas is introduced until the solution is saturated, after which the reaction product precipitated is filtered off under suction, washed with 50 ml of acetone and dried in vacuo at about 30°C. 12.8 g (90.5 percent of the theoretical yield) of the hydrochloride of the Schiff's base of 5-nitro-4-amino-1-naphthol and acetone are obtained in the form of pale yellow crystals, the product being identified by elemental analysis, NMR-spectrum and IR spectrum.

A mixture of 50 ml of 50 percent by weight aqueous acetic acid, 1 g of iron (III) chloride hexahydrate, 1.8 g of sodium chlorate and 0.5 ml of concentrated sulphuric acid, is introduced into the reaction vessel. 12.8 g of the hydrochloride, obtained as described above, are then introduced in small portions with stirring at about 70°C. After 20 minutes, the reaction mixture is cooled to 0°C, the pale yellow crystals are filtered off under suction, washed with a little cold methanol and dried at 50°C. 5-nitronaphthoquinone melting at 165°C is thus obtained in a yield of 9.1 g or 89 percent of the theoretical yield.

What is claimed is:

1. Process for producing 5-nitro-1,4-naphthoquinone which comprises reducing an oxime selected from the group of 8-nitro-1,4-naphthoquinone-1-oxime, 5-nitro-1,4-naphthoquinone-1-oxime and mixtures of the foregoing in a reaction medium selected from the group of water, an organic solvent and mixtures of water and an organic solvent in the presence of iron (II) ions and a hydrogen halide at a temperature in the range of from −20° to 100°C, and thereafter oxidizing the naphthol product formed, or the corresponding salt, optionally without intermediate isolation, at a temperature in the range of from −10° to 100°C to form the desired 5-nitro-1,4-naphthoquinone.

2. Process of claim 1 wherein reduction is carried out at a temperature in the range of from −5° to 70°C.

3. Process of claim 2 wherein the temperature is from 10° to 45°C.

4. Process of claim 1 wherein oxidation is carried out at a temperature in the range of from 20° to 80°C.

5. Process of claim 4 wherein the temperature is from 4° to 60°C.

6. Process of claim 1 wherein the iron (III) ions formed during reduction are used as an oxidizing agent for the oxidizing step.

* * * * *

UNITED STATES PATENT AND TRADEMARK OFFICE
CERTIFICATE OF CORRECTION

PATENT NO. : 3,931,255
DATED : January 6, 1976
INVENTOR(S) : Friedrich Dürholz et al It is certified that error appears in the above-identified patent and that said Letters Patent are hereby corrected as shown below:

Column 4, Line 61   Change "hydrchloric" to "hydrochloric".

Column 7, Line 50   In Example 20 "$H_2SO_4$" should read --$H_2SO_4$ (40%)--.

Column 10, line 26   "4° to 60°C" should read --40° to 60°C--

Signed and Sealed this twenty-fifth Day of May 1976

[SEAL]

Attest:

RUTH C. MASON
Attesting Officer

C. MARSHALL DANN
Commissioner of Patents and Trademarks